US00PP16454P3

(12) United States Plant Patent
Lintott

(10) Patent No.: US PP16,454 P3
(45) Date of Patent: Apr. 18, 2006

(54) ***CHRYSANTHEMUM* PLANT NAMED 'SYLLABUB PURPLE'**

(50) Latin Name: *Chrysanthemum morifolium*
Varietal Denomination: Syllabub Purple

(75) Inventor: Keith G. Lintott, Bognor Regis (GB)

(73) Assignee: Cleangro, Ltd., Chichester (GB)

( * ) Notice: Subject to any disclaimer, the term of this patent is extended or adjusted under 35 U.S.C. 154(b) by 73 days.

(21) Appl. No.: 10/993,289

(22) Filed: Nov. 18, 2004

(65) Prior Publication Data

US 2005/0120448 P1 Jun. 2, 2005

Related U.S. Application Data

(60) Provisional application No. 60/525,875, filed on Nov. 28, 2003.

(51) Int. Cl.
*A01H 5/00* (2006.01)

(52) U.S. Cl. ..... Plt./286

(58) Field of Classification Search ..... Plt./286
See application file for complete search history.

(56) References Cited

U.S. PATENT DOCUMENTS

PP11,852 P2 5/2001 Glicenstein ..... Plt./286

OTHER PUBLICATIONS

2002 Royal Vn Zanten Gardenmum catalog listing the variety 'Syllabub'. See, e.g. pp. 8 and 11 (photograph).

*Primary Examiner*—Anne Marie Grunberg
*Assistant Examiner*—Annette H Para
(74) *Attorney, Agent, or Firm*—Winston & Strawn, LLP

(57) ABSTRACT

A new variety of *Chrysanthemum* plant named 'Syllabub Purple' having a round, domed capitulum of bright purple, spoon petalled anemone type flowers.

1 Drawing Sheet

Latin name of the genus and species: Botanical classification: *Chrysanthemum morifolium.*

Variety denomination: The new *Chrysanthemum* variety denomination is 'Syllabub Purple.'

BACKGROUND OF THE INVENTION

The present invention comprises a new and distinct cultivar of *Chrysanthemum* botanically known as *Chrysanthemum morifolium*, and referred to by the cultivar name 'Syllabub Purple.'

'Syllabub Purple,' identified as 30620-7, was a whole plant mutation grown in a controlled planting of the unpatented variety 'Syllabub' in Cleangro Limited, Vinnetrow Road, Chichester, West Sussex PO20 1QD United Kingdom. The new *Chrysanthemum* variety 'Syllabub Purple' has been asexually reproduced by vegetative cuttings in Chichester, West Sussex, United Kingdom and the distinguishing characteristics are retained through successive generations of asexual reproduction.

BRIEF SUMMARY OF THE INVENTION

'Syllabub Purple' is a garden type of *Chrysanthemum* plant variety having a domed canopy of bright purple, uniform spoon petalled anemone type flowers.

Comparison with Parent

Plants of the new *Chrysanthemum* variety 'Syllabub Purple' are similar to the parent variety 'Syllabub' in plant habit and growth rate. In side-by-side comparisons in Chichester, West Sussex, United Kingdom, under commercial practice, plants of the new *Chrysanthemum* variety 'Syllabub Purple' differed from plants of the parent variety 'Syllabub' in the following characteristics.

1. The new *Chrysanthemum* variety 'Syllabub Purple' produces deep purple colored flowers whereas the parent 'Syllabub' produces lighter purple colored flowers.
2. Plants of the new *Chrysanthemum* variety 'Syllabub Purple' have shorter and smaller inflorescence than plants of the parent 'Syllabub.'
3. Plants of the new *Chrysanthemum* variety "Syllabub Purple" flower earlier than the parent variety 'Syllabub' under normal natural season conditions.

Comparison with Other Varieties

Plants of the new *Chrysanthemum* variety 'Syllabub Purple' are dissimilar to the variety 'Stacy,' U.S. Plant Pat. No. 11,852, in plant habit and growth rate. In side-by-side comparisons in Chichester, West Sussex, United Kingdom, under commercial practice, plants of the new *Chrysanthemum* variety 'Syllabub Purple' differed from 'Stacy' in the following characteristics.

1. The new variety 'Syllabub Purple' produces purple spoon tipped petals and purple cushioned flowers whereas 'Stacy' produces purple spoon tipped petals with a white base and yellow centered flowers.
2. Plants of the new variety 'Syllabub Purple' longer have and bigger inflorescence than plants of 'Stacy.'
3. Plants of the new *Chrysanthemum* variety 'Syllabub Purple' have a more domed and round shape than plants of the comparison variety 'Stacy.'

BRIEF DESCRIPTION OF ILLUSTRATIONS

Typical specimens of the plant and flowers for the new *Chrysanthemum* variety 'Syllabub Purple' are shown in the accompanying scanned image printed from a digital photograph. The colors shown are as true as possible within the usual limits of this kind of illustration.

FIG. 1 is a whole plant view of the new *Chrysanthemum* variety 'Syllabub Purple' grown in a pot. The plant shown in the illustration is 63 days from the commencement of planting outdoors in natural season conditions.

DETAILED BOTANICAL DESCRIPTION

The following description of the new *Chrysanthemum* variety 'Syllabub Purple' is of plants grown outside, natural season, in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 50° F. to 75° F. during the day under natural light conditions. The plants were grown outdoors in 4 liter pots using a loamless compost. No growth retardants were used. To produce a commercial product the plants may be pinched once with the center bud removed. The typical container size for commercial growth is 4 liters/8". It has been observed that the shelf life of the new variety is about 25 days with a response time of about 9 weeks natural season. The new variety is suitable for growth in a temperature range of 50° F. to 75° F.

The new variety may be produced as a garden pot plant. The following description is with respect to a plant produced as a pot plant. In the description of this new *Chrysanthemum* variety, color values have been taken from The Royal Horticultural Society Colour Chart (R.H.S.C.C.).

Plant

Plant type: Pot.
Habit: Free branching and spreading.
Height: 40 cm–55 cm.
Width: 40 cm–50 cm.
Stem: Length: 9 cm–11 cm.
- *Diameter.*—0.5 cm–0.7 cm.
- *Texture.*—Smooth slightly pubescent.
- *Color.*—Near 152 C.

Branching characteristics: Free branching and spreading.
Length of lateral branches: 8 cm–14 cm.
Number of breaks from pinch: 7–12.
Response time: Near 9 weeks natural.
Vigor: Medium.
Shelf life: Near 25 days.
Disease (susceptibility/resistance observed): None observed to date.
Pest (susceptibility/resistance observed): None observed to date.
Growth retardant type and treatment: No treatment necessary. The plants were grown for 9 weeks in natural season conditions.
Propagation:
- *Type.*—Vegetative Propagation via Stem Cuttings.
- *Time to rooting.*—12 days with soil temperatures of 70° F.
- *Rooting habit.*—Fine and Fibrous.

Foliage

Number of leaves per lateral branch: 5–9.
Compound or single: Single.
Arrangement of leaves: Alternate.
- *Shape of leaf.*—Typically 5 lobed ovate.
- *Size of leaf.*—Width: 2 cm–3 cm. Length: 3 cm–5 cm.
- *Leaf apex.*—Acute.
- *Base.*—Obtuse.
- *Attachment.*—Petioled.
- *Aspect.*—Slightly undulating.
- *Margin.*—Palmately lobed.
- *Surface characteristics.*—Top: Smooth/shiny. Bottom: Slightly pubescent.

Petiole:
- *Color.*—Near 139A.
- *Length.*—0.7 cm–1.2 cm.

Venation: Net, mid vein prominent at underside.
- *Color.*—Upper side: near 139C. Under side: near 138C.

Color:
- *Mature leaf, upper side.*—Near 137A; under side: near 137C.
- *Young leaf, upper side.*—Near 137A; under side: near 137C.

Flower

Flower appearance: Matte.
Flower type: Anemone.
Flower form: Slightly cupped.
Flower shape: Round.
Flowering habit: Cyme.
Number of blossoms per branch: 5–9.
Inflorescence form: Corymbiform.
- *Depth of fully expanded blossoms.*—1 cm–1.5 cm.
- *Diameter of fully expanded blossoms.*—5 cm–6 cm.
- *Anemone center diameter.*—1.5 cm–2 cm.

Phyllaries:
- *Number.*—20–23.
- *Color.*—Near 138B.
- *Length.*—0.6 cm–0.9 cm.
- *Width.*—0.15 cm–0.3 cm.
- *Texture/appearance.*—Shiny/Slightly pubescent.

Peduncle: Peduncle length is shortest at the terminal flower and progressively longer moving down the stem; longest length is on average 13 (cm), shortest length is on average 7 (cm).
- *Length.*—7 cm–13 cm.
- *Color.*—Near 138C.
- *Surface.*—Pubescent.
- *Habit.*—Very slightly curving.
- *Strength.*—Strong.

Ray florets:
- *Form/shape.*—Spoon — Straight.
- *Texture/appearance.*—Matte.
- *Number per flower.*—65–75.
- *Length.*—2 cm–3 cm; Width: 0.4 cm–0.6 cm.
- *Apex.*—Round.
- *Base.*—Tubular.
- *Margin.*—Entire.

Disc florets:

*Form/shape*.—Five sided tubular.
*Texture/appearance*.—Matte.
*Number per flower*.—125–140.
*Length*.—0.7 cm–0.9 cm; Width: 0.1 cm–0.2 cm.
*Diameter of disc*.—1.5 cm–2 cm.

Fragrance: Slight.

Flower bud: Near 137A.

*Length*.—0.5 cm–0.7 cm.
*Diameter*.—0.8 cm–1 cm.
*Form/shape*.—Round/Flattened.

General flower color:

1. *Ray florets, upper side*.—Immature: near 63C. Mature: near 58B. Older/Fading: near 58C.
2. *Ray florets, under side*.—Immature: near 63C. Mature: near 58B. Older/Fading: near 58C.
3. *Disc florets*.—Immature: near 162C. Mature: near 163B. Older/Fading: near 163C.
4. *Bud*.

Flower progression with age: Flowers fade uniformly and slightly with age.

Reproductive Organs

Gynoecium present on ray florets.

Ray florets per individual flower:

*Pistil number*.—20–23 observed.
*Stigma color*.—Near 14B.
*Stigma shape*.—Forked.
*Style color*.—Near 151B.
*Style length*.—0.15 cm–0.2 cm.

Disc florets: None observed.

Androecium present on disc florets only.

Disc florets per individual flower:

*Stamen number*.—55–60 observed.
*Anther shape*.—Globular.
*Anther color*.—Near 14A.
*Pollen color*.—Near 14B.

Pollen quantity: Medium.

Fruit and seeds: None observed.

What is claimed is:

1. A new and distinct variety of *Chrysanthemum* plant, substantially as described and illustrated herein.

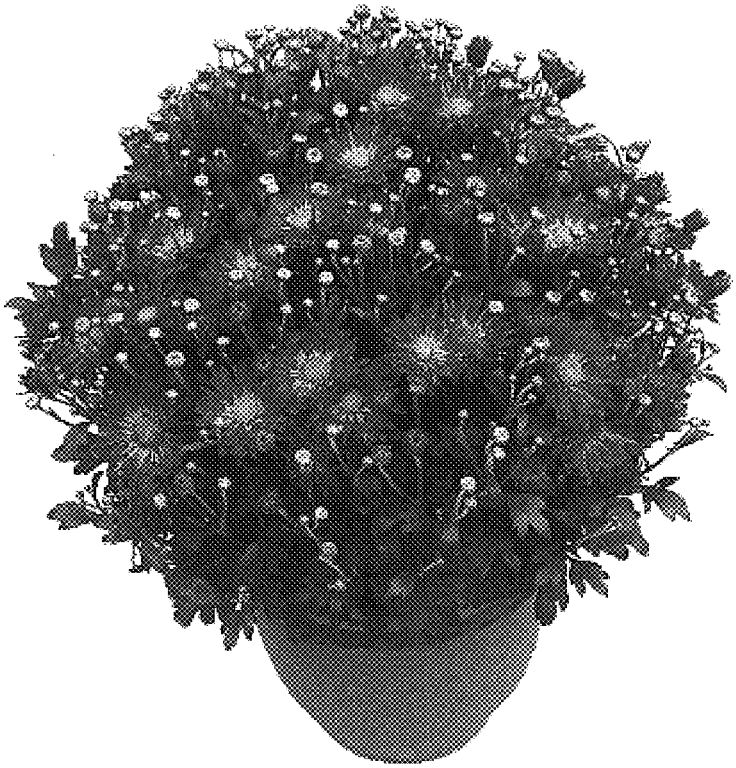

* * * * *